US009227913B2

(12) United States Patent
Longuet et al.

(10) Patent No.: US 9,227,913 B2
(45) Date of Patent: Jan. 5, 2016

(54) PREVENTION OR SUPPRESSION OF CRYSTALLISATION OF BORIC ACID PRESENT IN AN AQUEOUS PHASE

(71) Applicant: Commissariat a l'energie atomique et aux energies alternatives, Paris (FR)

(72) Inventors: Laurence Longuet, Veigne (FR); Laurence Autissier, Saint Avertin (FR); Alix Briere, Tours (FR)

(73) Assignee: Commissariat a L'Energie Atomique et aux Energies Alternatives, Paris (FR)

( * ) Notice: Subject to any disclaimer, the term of this patent is extended or adjusted under 35 U.S.C. 154(b) by 0 days.

(21) Appl. No.: 14/403,526

(22) PCT Filed: May 27, 2013

(86) PCT No.: PCT/EP2013/060879
§ 371 (c)(1),
(2) Date: Nov. 24, 2014

(87) PCT Pub. No.: WO2013/178589
PCT Pub. Date: Dec. 5, 2013

(65) Prior Publication Data
US 2015/0158810 A1 Jun. 11, 2015

(30) Foreign Application Priority Data

May 29, 2012 (FR) ...................................... 12 54930

(51) Int. Cl.
| | | |
|---|---|---|
| C07C 215/10 | (2006.01) |
| C01B 35/10 | (2006.01) |
| C07C 55/08 | (2006.01) |
| C07C 31/20 | (2006.01) |
| C07C 35/16 | (2006.01) |

(52) U.S. Cl.
CPC ........... *C07C 215/10* (2013.01); *C01B 35/1054* (2013.01); *C07C 31/205* (2013.01); *C07C 35/16* (2013.01); *C07C 55/08* (2013.01)

(58) Field of Classification Search
CPC .......................... C01B 35/1054; C01B 35/109
See application file for complete search history.

(56) References Cited

U.S. PATENT DOCUMENTS

| 5,928,672 A | 7/1999 | Hammons et al. |
| 5,939,038 A * | 8/1999 | Wilkomirsky ................ 423/276 |
| 2008/0305351 A1* | 12/2008 | Schubert .................... 428/537.1 |

FOREIGN PATENT DOCUMENTS

| GB | 2 446 038 A | 7/2008 |
| WO | WO 2005/094545 A2 | 10/2005 |
| WO | WO 2012011056 * | 1/2012 ............. C09J 103/02 |

OTHER PUBLICATIONS

Database CAPLUS in STN, Acc. No. 1931:3940, Davis, Journal of Chemical Education (1930), 7, pp. 2675-2686 (abstract).*
International Preliminary Examination Report for PCT/EP2013/060879 dated Dec. 4, 2014, with English language translation.
Taylor et al.; "Triol Borates and Aminoalcohol Derivatives of Boric Acid: Their Formation and Hydrolysis"; Polyhedron, vol. 15, No. 19, pp. 3261-3270, Jun. 1, 1996.
International Search Report for International Application No. PCT/EP2013/060879 dated Aug. 7, 2013.
French Search Report for French Patent Application No. 1254930 dated Feb. 12, 2013.

* cited by examiner

*Primary Examiner* — Brian J Davis
(74) *Attorney, Agent, or Firm* — Miles & Stockbridge P.C.

(57) ABSTRACT

A method for preventing the crystallization of boric acid present in an aqueous phase, or for suppressing this crystallization when crystallization has already been initiated, including the addition of at least one compound comprising at least two hydroxyl functions, the compound being selected from alcohols, aminoalcohols, carboxylic acids, and hydroxy acids.

9 Claims, 1 Drawing Sheet

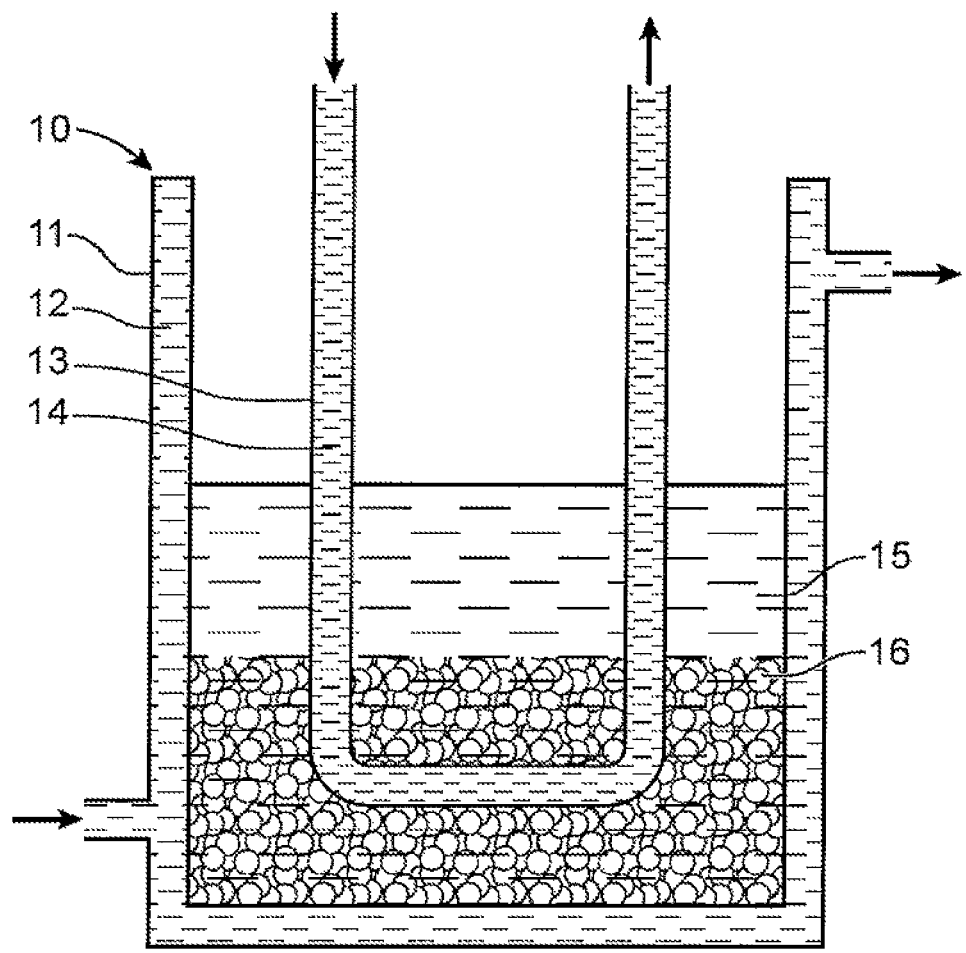

PREVENTION OR SUPPRESSION OF CRYSTALLISATION OF BORIC ACID PRESENT IN AN AQUEOUS PHASE

TECHNICAL FIELD

The invention relates to the use of at least one particular compound for preventing crystallization of boric acid present in an aqueous phase, or for suppressing this crystallization when the crystallization had already been initiated.

The invention finds application, generally, in all the fields in which boric acid may be used and, in particular, in fields in which it is necessary to rapidly have available aqueous phases containing boric acid which do not include boric acid crystals, for example in the nuclear industry field.

DISCUSSION OF THE TECHNICAL PROBLEM

Boric acid, further called hydrogen borate, boracic acid or orthoboric acid is a chemical compound with the empirical formula $H_3BO_3$ which is classified among weak Lewis acids.

It is commonly used in the steel and metal industries, as a flux component for welding or for brazing; in the textile and polymer industries, as a flame retardant for cellulose fibers and for plastics; in the wood industry, for its antifungal and insecticidal properties; or further in the nuclear industry, for example as a neutron absorbing agent.

It is further used in products for the general public for its biocidal properties, notably in personal care, cosmetic, or further anti-septic products.

Boric acid appears in the form of colorless crystals or as a white powder which are relatively not very soluble in water, the mass solubility of boric acid in water having the theoretical value of 47.2 grams per liter (g/L) at a temperature of 20 degrees Celsius (° C.) and at ambient pressure.

This low solubility of boric acid, although varying according to parameters such as pH and temperature of the thereby formed aqueous phase, represents a major drawback when a large amount of boric acid dissolved in an aqueous phase has to be rapidly available.

Further, in the case of aqueous phases with very high concentrations of boric acid, an example of that being aqueous solutions, saturated and oversaturated with boric acid, the establishment of a concentration and pH gradient within these phases may further be observed, this gradient still further promoting the crystallization phenomenon which is then observed after only a few days.

The inventors therefore set the objective of finding a solution to the problem posed by the crystallization of boric acid present in an aqueous phase, this crystallization being able to have been already initiated.

DISCUSSION OF THE INVENTION

This goal is achieved by the invention, which firstly proposes the use of at least one compound comprising at least two hydroxyl functions, the compound being selected from alcohols, aminoalcohols, carboxylic acids and hydroxyacids, for preventing crystallization of boric acid present in an aqueous phase, or for suppressing this crystallization when this crystallization has already been initiated.

It is specified that by the expression "aqueous phase", is meant a phase for which the solvent is exclusively or quasi-exclusively made up of water, i.e. a phase in which the volume proportion of water within the solvent of the aqueous phase is at least equal to 90 percent (%), still better, equal to 95% and, preferably, equal to 100%, and wherein the boric acid present in the phase may crystallize, or wherein the crystallization phenomenon has already been initiated.

Thus, according to the invention, the use of such a compound gives the possibility of preventively precluding crystallization of boric acid present in an aqueous phase.

In a complementary approach, the use of such a compound also allows suppression or, at the very least, strong reduction, curatively, of the presence of boric acid crystals already formed in an aqueous phase containing boric acid, by promoting solubilization of these boric acid crystals.

Given that the compound comprising at least two hydroxyl functions is intended to ensure stabilization of aqueous phases containing boric acid, this compound is preferably selected from compounds in which the total number of carbon atoms does not exceed eight, so as to have sufficient hydrophilicity so as to be able to be used in an aqueous phase.

In which case, the compound may notably be selected from polyhydroxylated $C_2$-$C_8$ alcohols which are defined as organic compounds including at least two hydroxyl groups, each of them being bound to a tetragonal carbon atom and up to two hydroxyl groups may be bound to a same tetragonal carbon. These polyhydroxylated alcohols may be saturated or unsaturated, as well as with a linear, a branched or a cyclic chain. Advantageously, these alcohols do not include any functional group (s) other than hydroxyl groups. Mention may notably be made, as examples, of ethylene glycol, propylene glycol, 2,2-dimethylpropane-1,3-diol, pentaerythritol or further myo-inositol.

The compound may further be selected from polyhydroxylated $C_2$-$C_8$ aminoalcohols, which are defined as polyhydroxylated $C_2$-$C_8$ alcohols including at least one amine function —$NR^1R^2$, wherein $R^1$ and $R^2$ each independently of each other refer to a hydrogen atom or to an alkyl group having an adjusted number of carbon atoms so that the polyhydroxylated aminoalcohol is a $C_2$-$C_8$ aminoalcohol. These polyhydroxylated aminoalcohols may be saturated or unsaturated, as well as with a linear, a branched or a cyclic chain, such as for example diethanolamine, triethanolamine, 2-amino-2-(hydroxymethyl)-propane-1,3-diol (or <<Tris>>) or further 2-[bis-(2-hydroxyethyl)-amino]-2-(hydroxy-methyl)-propane-1,3-diol (or <<Bis-Tris>>).

Document WO 2005/094545 A2 describes a method for inhibiting crystallization of boric acid. This method comprises the following steps:
dissolving boric acid in a mixture formed with water and a vitrifying agent in order to form an aqueous mixture,
drying this aqueous mixture in order to form a vitreous residue containing boric acid.

The vitrifying agent is selected from aminoalcohols and amino acids. Among the aminoalcohols which may be used as a vitrifying agent, tris(hydroxylmethyl)aminomethane, which corresponds to 2-amino-2-(hydroxymethyl)-propane-1,3-diol or Tris, is described.

However, it clearly emerges from the teaching of document WO 2005/094545 A2 that the applied method gives the possibility of obtaining inhibition of the crystallization of boric acid in the vitreous residue resulting from the drying step. An inhibition of the crystallization of boric acid in the aqueous mixture resulting from the dissolution step is, on the other hand, neither described nor even suggested in this document of the state of the art.

The compound may further be selected from $C_2$-$C_8$ dicarboxylic acids, these acids may be saturated or unsaturated, as well as with a linear, a branched or a cyclic chain. Advantageously, these dicarboxylic acids do not include any functional group(s) other than hydroxyl groups. As examples, mention may notably be made of oxalic, maleic or further malonic acids.

The compound may finally be selected from $C_2$-$C_8$ hydroxyacids, which are defined as $C_2$-$C_8$ carboxylic acids including at least one hydroxyl group different from the one of the carboxylic acid function (s) borne by the compound. These hydroxyacids may be saturated or unsaturated, as well as with a linear, a branched or a cyclic chain, such as for example mevalonic or quinic acids.

Preferentially, the compound comprising at least two hydroxyl functions includes from two to six hydroxyl functions.

In which case, the compound comprising at least two hydroxyl functions is advantageously selected from maleic acid, 2,2-dimethylpropane-1,3-diol, 2-amino-2-(hydroxymethyl)-propane-1,3-diol, 2-[bis-(2-hydroxyethyl)-amino]-2-(hydroxymethyl)-propane-1,3-diol, myo-inositol and pentaerythritol.

Among these compounds, 2-amino-2-(hydroxy-methyl)-propane-1,3-diol (or «Tris»), 2-[bis-(2-hydroxyethyl)-amino]-2-(hydroxymethyl)-propane-1,3-diol (or «Bis-Tris») and pentaerythritol are more preferred.

According to the invention, the use of a compound including two hydroxyl functions is especially recommended for treating aqueous phases, saturated or oversaturated with boric acid, and which may be kept under uncontrolled temperature conditions, such as those prevailing in warehousing sites.

Consequently, the boric acid mass concentration in the aqueous phase is preferably at least equal to the value of the mass solubility of boric acid at the temperature which is exhibited by this aqueous phase containing boric acid.

Within the scope of the invention, it is specified that this mass concentration is determined by considering boric acid in all its physical forms, both the boric acid dissolved in the aqueous phase and the boric acid which is possibly present in crystallized form within the aqueous phase.

Further, the molar ratio of the compound comprising two hydroxyl functions to the whole of the boric acid either partly or completely dissolved in the aqueous phase containing boric acid is preferentially comprised in a range from 0.1/1 to 0.7/1.

Moreover, within the scope of their investigations, the inventors were able to show an influence of the form in which the compound comprising at least two hydroxyl functions is used.

Indeed, they ascertained that the effect of reducing or suppressing crystallization of the boric acid present in an aqueous phase is more pronounced when the compound is added to this aqueous phase in a solid form rather than in liquid form, and this even in the absence of any step (stirring, for example) directed to promoting dissolution of the compound in the aqueous phase containing boric acid.

Also, the compound comprising at least two hydroxyl functions is preferably added in solid form to the aqueous phase containing boric acid.

Nevertheless, it is also possible to add the compound comprising at least two hydroxyl functions to the aqueous phase containing boric acid, in liquid form and notably in the form of a solution which is obtained by dissolving the compound beforehand in the same solvent as the one of the aqueous phase.

The use of a compound including at least two hydroxyl functions, as the use which has just been described, is in particular applicable in the field of the nuclear industry, for example for purposes of stabilizing aqueous phases containing boric acid intended to be used as neutron absorbing media.

Other features and advantages of the invention will become apparent from the additional description which follows, which relates to examples of compounds which may be used within the scope of the invention, and to the demonstration of the properties for preventing or suppressing crystallization of boric acid which are allowed by these compounds, this additional description referring to the appended figure.

It is obvious that these examples are only given as an illustration of the objects of the invention and by no means are a limitation of these objects.

SHORT DESCRIPTION OF THE DRAWINGS

The single FIGURE is an illustration of the device used for the tests for demonstrating the properties for preventing or suppressing crystallization of boric acid which are made possible by the invention.

DETAILED DISCUSSION OF PARTICULAR EMBODIMENTS

Method:

The tests described in the examples hereafter are conducted by means of a device of the type of the one illustrated in the single FIGURE.

The device consists of a beaker 10 with a double glass wall 11, inside which flows a heat transfer fluid 12. The beaker 10 also contains a U-shaped metal tube 13, which contains a circulating heat transfer fluid 14.

The temperatures of the heat transfer fluids 12 and 14 are each adjusted independently of the other, by a heat generator (not shown in the single FIGURE).

However, the temperature of the heat transfer fluid 14 is adjusted so that it is always strictly less than that of the heat transfer fluid 12, typically lower by 1° C. to 10° C. If it is assumed that heat conduction of the material making up the metal tube 13 occurs without any notable loss, the walls of the tube 13 blasts thus form a so-called «cold» element.

Two temperature cycles may be applied to an aqueous phase 15 containing boric acid, which is poured into the beaker 10.

A temperature cycle «N» is thus defined, for example of 28 days, having:

periods with low thermal variations, during which the temperatures of the heat transfer fluids 12 and 14 are (20±2)° C. and (19±2)° C. respectively, for example respectively having the values of 18° C. and 17° C. simultaneously, which have the role of facilitating the formation of a boric acid seed by nucleation in the investigated aqueous phase; and periods with large thermal variations, and during which the temperatures of the heat transfer fluids 12 and 14 are (16±4)° C. and (14±4)° C. respectively, for example respectively having the values of 14° C. and 10° C. simultaneously, which have the role of accelerating crystallization of boric acid within the investigated aqueous phase.

A temperature cycle «P» (or with a penalty) is further defined, for example of 28 days, having:

periods of low thermal variations, during which the temperatures of the heat transfer fluids 12 and 14 are (20±2)° C. and (19±2)° C. respectively, for example respectively having the values of 18° C. and 17° C. simultaneously, which have the role of facilitating the formation of a boric acid seed by nucleation in the investigated aqueous phase;

periods of large thermal variations at temperatures above room temperature, during which the temperatures of the heat transfer fluids 12 and 14 are thus $(35\pm15)°$ C. and $(30\pm10)°$ C. respectively, for example respectively having the values of 50° C. and 40° C. simultaneously; and periods of large thermal variations at temperatures below room temperature, during which the temperatures of the heat transfer fluids 12 and 14 are thus $(12\pm8)°$ C. and $(10\pm9)°$ C. respectively, for example respectively having the values of 3° C. and 1° C. simultaneously, which have the role of accelerating crystallization of boric acid within the investigated aqueous phase.

Regardless of the relevant temperature cycle, a crystallization rate is defined at the end of one of these temperature cycles, which corresponds to the ratio of the mass of boric acid crystals measured at the end of this cycle, to the total initially introduced mass of boric acid.

It is recalled that, in the examples hereafter, the mass concentration in a liquid solution of a species, for example called A, is expressed independently of the fact that this species A is partly or completely dissolved in this solution.

Example 1

Six aqueous phases noted as $P_i$ (the index <<i>> designating an integer comprised between 1 and 6) are formed, each by putting into contact:

an aqueous phase of Tris, with a mass concentration $C_i$ and in which the Tris is in a completely dissolved form; and an aqueous phase containing boric acid with a mass concentration $C'_i$.

For each concentration $C_i$, the amount $n_i$ of Tris contained in one liter of Tris aqueous phase is calculated.

Also for each concentration $C'_i$, the amount $n'_i$ of boric acid contained in one liter of aqueous phase containing boric acid is calculated.

For each phase $P_i$, a (dimensionless) molar ratio $R_i$ is defined which corresponds to the ratio $n_i/n'_i$. Further information is reported in Table 1.

TABLE 1

| Aqueous phase | $C_i$ (g/L) | $C'_i$ (g/L) | $R_i$ (∅) |
|---|---|---|---|
| $P_1$ | 100 | 1490 | 0.034 |
| $P_2$ | 500 | 1490 | 0.172 |
| $P_3$ | 50 | 540 | 0.047 |
| $P_4$ | 100 | 550 | 0.093 |
| $P_5$ | 200 | 540 | 0.189 |
| $P_6$ | 500 | 550 | 0.464 |

Each of the aqueous phases $P_i$ is subject to a temperature cycle N for 28 days.

At the end of this period, it is seen that no crystallization occurred within any of the aqueous phases $P_1$ to $P_6$.

The crystallization rates are thus equal to zero for the whole of the phases $P_1$ to $P_6$, although the following observations may be made:

on the one hand, in the case when the phase $P_2$ is prepared and homogenized before storage, the non-dissolved boric acid (because of oversaturation) which is observed before completing the temperature cycle N, is half-dissolved at the end of this cycle, this, without any additional crystallization, and the phase $P_2$ then has a slightly cloudy or <<cotton-like>> visual aspect; and on the other hand, in the case when the phase $P_6$ is prepared and homogenized before storage, the non-dissolved boric acid (because of oversaturation) which is re-dissolved before completing the temperature cycle N, does not crystallize at the end of the cycle.

Example 2

An aqueous phase $P_7$ containing boric acid, with a mass concentration of 550 g/L, is subject to a first temperature cycle N for 28 days.

At the end of this period, a setting of the aqueous phase $P_7$, due to crystallization of boric acid, is observed. The crystallization rate measured for $P_7$ is 7% on average.

An aqueous phase $P_{7'}$ is then made by introducing into the aqueous phase $P_7$ and without stirring, a mass of 80 g of Tris in solid form.

In a few hours, a reduction in the amount of crystallized boric acid is observed.

A second temperature cycle N of 28 days is then applied to the aqueous phase $P_{7'}$, at the end of which no additional crystallization is observed. The crystallization rate for $P_{7'}$ is then established at 3.1%.

An appreciable reduction in the crystallization of boric acid in an aqueous phase containing boric acid is thus observed in the presence of Tris introduced curatively, in the case of a temperature cycle N.

Example 3

An aqueous phase $P_8$ is formed by putting into contact an aqueous phase containing boric acid with a mass concentration of 1490 g/L, and an aqueous phase of Tris with a mass concentration of 25 g/L and in which Tris is in the completely dissolved form.

An aqueous phase $P_9$ is formed by putting into contact an aqueous phase containing boric acid with a mass concentration of 1490 g/L, and Tris in solid form and introduced as an amount of 25 g per liter of aqueous phase containing boric acid.

Each of the aqueous phases $P_8$ and $P_8$ is subject to a temperature cycle N for 28 days at the end of which the crystallization rates are established at 3.2% for $P_8$, and 0.7% for $P_9$.

An appreciable reduction in the crystallization of boric acid in an aqueous phase containing boric acid is thus observed when Tris is used, in the case of a temperature cycle N, this reduction being further pronounced when Tris is introduced in solid form.

Example 4

An aqueous phase $P_{10}$, containing boric acid with a mass concentration of 1490 g/L, is formed.

An aqueous phase $P_{11}$ is formed by putting into contact an aqueous phase containing boric acid with a mass concentration of 1490 g/L, and pentaerythritol in solid form and introduced as an amount of 75 g per liter of aqueous phase containing boric acid.

Each of the aqueous phases $P_{10}$ and $P_{11}$ is subject to a temperature cycle N for 28 days, at the end of which cycles the crystallization rates are established at 7.2% for $P_{10}$, and 2.3% for $P_{11}$.

An appreciable reduction in the crystallization of boric acid in an aqueous phase containing boric acid is thus observed in the presence of pentaerythritol, in the case of a temperature cycle N.

Example 5

An aqueous phase $P_{12}$, containing boric acid with a mass concentration of 1490 g/L, is formed.

An aqueous phase $P_{13}$ is formed by putting into contact an aqueous phase containing boric acid, with a mass concentration of 1490 g/L, and solid pentaerythritol, introduced as an amount of 75 g/L of aqueous phase containing boric acid.

Each of the aqueous phases $P_{12}$ and $P_{13}$ is subject to a temperature cycle P during 28 days, at the end of which cycles the crystallization rates are established at 20.4% for $P_{12}$, and 4.0% for $P_{13}$.

A large reduction of the crystallization of boric acid in an aqueous phase containing boric acid is thus observed in the presence of pentaerythritol, in the case of a temperature cycle P.

The invention claimed is:

1. A method comprising:
   providing an aqueous phase containing boric acid; and
   preventing crystallization of said boric acid in said aqueous phase or suppressing said crystallization when crystallization has already been initiated by adding to said aqueous phase at least one compound comprising at least two hydroxyl functions, said at least one compound being selected from alcohols, amino-alcohols, carboxylic acids, and hydroxyacids, said at least one compound promoting solubilization of said boric acid in said aqueous phase.

2. The method according to claim 1, wherein said at least one compound comprising at least two hydroxyl functions includes a total number of carbon atoms which is at most equal to eight.

3. The method according to claim 2, wherein said at least one compound comprising at least two hydroxyl functions includes from 2 to 6 hydroxyl functions.

4. The method according to claim 3, wherein said at least one compound comprising at least two hydroxyl functions is selected from maleic acid, 2,2-dimethylpropane-1,3-diol, 2-amino-2-(hydroxylmethyl)-propane-1,3-diol, 2-[bis-(2-hydroxyethyl)-amino]-2-(hydroxymethyl)-propane-1,3-diol, myo-inositol, and pentaerythritol.

5. The method according to claim 4, wherein said at least one compound comprising at least two hydroxyl functions is selected from 2-amino-2-(hydroxylmethyl)-propane-1,3-diol, 2-[bis-(2-hydroxyethyl)-amino]-2-(hydroxymethyl)-propane-1,3-diol, and pentaerythritol.

6. The method according to claim 1, wherein a mass concentration of said boric acid in said aqueous phase is at least equal to a value of a mass solubility of boric acid at a temperature which is exhibited by said aqueous phase containing said boric acid.

7. The method according to claim 1, wherein a molar ratio of said at least one compound comprising at least two hydroxyl functions to said boric acid in said aqueous phase is from 0.1/1 to 0.7/1.

8. The method according to claim 1, wherein said at least one compound comprising at least two hydroxyl functions is added in solid form to said aqueous phase containing said boric acid.

9. The method according to claim 1, wherein said at least one compound comprising at least two hydroxyl functions is added in liquid form to said aqueous phase containing said boric acid.

* * * * *